(12) United States Patent
Herrero et al.

(10) Patent No.: US 9,591,867 B2
(45) Date of Patent: *Mar. 14, 2017

(54) COMPOSITIONS OF ABSCISIC ACID FOR ANIMAL HEALTH

(71) Applicant: Valent BioSciences Corporation, Libertyville, IL (US)

(72) Inventors: Maria Pilar Herrero, Lake Forest, IL (US); Warren E. Shafer, Libertyville, IL (US)

(73) Assignee: Valent BioSciences Corporation, Libertyville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/463,987

(22) Filed: Aug. 20, 2014

(65) Prior Publication Data

US 2014/0364501 A1 Dec. 11, 2014

Related U.S. Application Data

(62) Division of application No. 13/236,444, filed on Sep. 19, 2011, now abandoned.

(60) Provisional application No. 61/384,020, filed on Sep. 17, 2010.

(51) Int. Cl.
*A61K 31/19* (2006.01)
*A23K 1/16* (2006.01)
*A61K 31/192* (2006.01)

(52) U.S. Cl.
CPC .......... *A23K 1/1609* (2013.01); *A23K 20/105* (2016.05); *A23K 50/75* (2016.05); *A23K 50/80* (2016.05); *A23L 33/105* (2016.08); *A61K 31/19* (2013.01); *A61K 31/192* (2013.01)

(58) Field of Classification Search
CPC .............................. A23K 50/00; A23K 20/105
See application file for complete search history.

(56) References Cited

U.S. PATENT DOCUMENTS

| 4,209,530 | A | | 6/1980 | Visscher |
| 4,434,180 | A | | 2/1984 | Visscher |
| 5,632,995 | A | * | 5/1997 | Wade ............... A61K 35/74 |
| | | | | 424/115 |
| 2006/0292215 | A1 | | 12/2006 | Romero M |
| 2007/0184060 | A1 | | 8/2007 | Bassaganya-Riera et al. |
| 2008/0242635 | A1 | | 10/2008 | Elshout et al. |
| 2010/0216883 | A1 | | 8/2010 | Bassaganya-Riera et al. |

FOREIGN PATENT DOCUMENTS

| WO | WO 2006/111546 | * 10/2006 |
| WO | WO2007/042983 | 4/2007 |

OTHER PUBLICATIONS

Milborrow, "The chemistry and physiology of abscisic acid", Am. Rev. Plant Physiol. 1974, 25 pp. 259-307.
Liu, Phenotyping of mice with extremely low PPARgamma level, 2008 [online], [Retrieved on Jan. 6, 2012].
Berge "Pharmaceutical salts", Journal of Pharmaceutical Sciences, Jan. 1977, vol. 66, No. 1, pp. 1-19.

* cited by examiner

*Primary Examiner* — Sahar Javanmard
(74) *Attorney, Agent, or Firm* — Wood, Phillips, Katz, Clark & Mortimer

(57) ABSTRACT

The invention relates to compositions comprising abscisic acid, and/or salts, derivatives and analogs thereof, and methods of using the same for improving the health and survival of animal offspring.

3 Claims, No Drawings

COMPOSITIONS OF ABSCISIC ACID FOR ANIMAL HEALTH

FIELD OF THE INVENTION

The present invention generally relates to compositions comprising abscisic acid, and/or salts, derivatives and analogs thereof, and methods of their preparation and administration for and/or nutraceutical use in animals.

BACKGROUND OF THE INVENTION

Abscisic acid is a naturally occurring plant hormone and a safe, nontoxic substance. The chemistry and physiology of abscisic acid and its analogs is described by Milborrow, Ann. Rev. Plant Physiol. 1974, 25, 259-307. The naturally occurring enantiomeric form of abscisic acid is (S)-(+)-abscisic acid. The stereochemistry of the side chain of the major part of naturally occurring abscisic acid is 2-cis-,4-trans-, since that is the isomer that is produced biosynthetically by all green plants and some microorganisms.

Certain salts of abscisic acid, and/or derivatives and analogs thereof, as described in U.S. application Ser. No. 12/011,846, 12/011,825, 61/083,202, 61/083,203 and PCT/US08/01203, however, have demonstrated high concentrations of abscisic acid in their compositions, and are incorporated herein.

Commercial formulations comprising abscisic acid are used in agriculture and horticulture on or around crops and plants for improving stress tolerance, slowing the growth rate, and adjusting flowering phase. Abscisic acid has also been reported to possess insect inhibition qualities. See U.S. Pat. Nos. 4,434,180 and 4,209,530. Others have reported potential medicinal properties of abscisic acid, for example US patent application No. 2006/0292215 discloses methods of using abscisic acid for anti-cancer purposes, and international application No. WO 2007/042983 discloses anti-inflammatory activity of abscisic acid. Contents of these patents are incorporated by reference.

Here, Applicants have surprisingly discovered that abscisic acid, and/or salts, derivatives and analogs thereof, have nutraceutical properties in animals.

SUMMARY OF THE INVENTION

The present invention is generally directed to compositions comprising abscisic acid, and/or salts, derivatives and analogs thereof (collectively referred to as "ABA" herein), of which (S)-(+)-abscisic acid is one enantiomer (hereinafter "S-ABA"), and methods of their use as nutraceuticals. Applicants found that compositions of ABA can be used to treat various ailments, and may also be used as nutraceuticals.

Compositions of the present invention generally comprise ABA. Other components which enhance the biological activity of the ABA may optionally be included.

Another embodiment of the present invention is directed to treatment for diabetes including methods of reducing glucose levels and methods of decreasing triglyceride levels in blood comprising administering to an animal a therapeutically effective amount of ABA.

In yet another embodiment, the present invention is directed to reproduction and more specifically to methods of increasing post-natal survival rates and weight comprising administering to an animal in need thereof, or lactating parent of animal in need thereof, a therapeutically effective amount of ABA.

Another embodiment of the present invention is directed to methods of increasing immunological function comprising administering to an animal in need thereof a therapeutically effective amount of ABA. This immunological effect may be, at least in part, indicated via the observed reduction in size of the spleen, as a number of conditions—from infections to liver disease and some cancers—can cause an enlarged spleen.

Finally in another embodiment, the present invention is directed to enhancing alertness and the treatment of attention deficit disorder comprising administering to an animal a therapeutically effective amount of ABA.

The disclosed embodiments are simply exemplary embodiments of the inventive concepts disclosed herein and should not be considered as limiting, unless the claims expressly state otherwise.

DETAILED DESCRIPTION OF THE INVENTION

The present invention is generally directed to compositions comprising ABA, of which S-ABA is one enantiomer, and methods of their use as nutraceuticals. Applicants found that compositions of ABA can be used to treat various ailments, as well be used as nutraceuticals, in infant formula or as a food ingredient.

Preferred ABA analogs and derivatives are defined by Structures 1, 2, and 3, wherein for Structure 1:

the bond at the 2-position of the side chain is a cis- or trans-double bond, the bond at the 4-position of the side chain is a trans-double bond or a triple bond, the stereochemistry of the alcoholic hydroxyl group is S—, R— or an R,S-mixture, the stereochemistry of the R1 group is in a cis-relationship to the alcoholic hydroxyl group, $R_1$=ethynyl, ethenyl, cyclopropyl, or trifluoromethyl, and $R_2$=hydrogen or lower alkyl

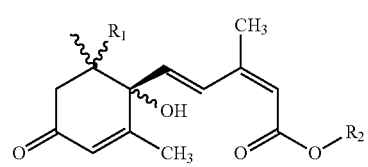

Structure 1 wherein lower alkyl is defined as an alkyl group containing 1 to 4 carbon atoms in a straight or branched chain, which may comprise zero or one ring or double bond when 3 or more carbon atoms are present.

For Structure 2:

the bond at the 2-position of the side chain is a cis- or trans-double bond, the bond at the 4-position of the side chain is a triple bond, the stereochemistry of the alcoholic hydroxyl group is S—, R— or an R,S-mixture, R1=hydrogen or lower alkyl Structure 2

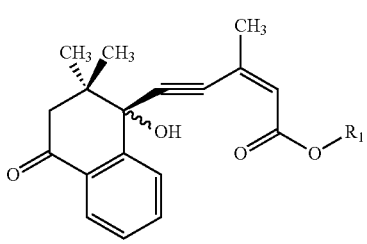

wherein lower alkyl is defined as an alkyl group containing 1 to 4 carbon atoms in a straight or branched chain, which may comprise zero or one rind or double bond when 3 or more carbon atoms are present.

For Structure 3:
the bond at the 2-position of the side chain is a cis- or trans-double bond,
the bond at the 4-position of the side chain is a trans-double bond,
the stereochemistry of the alcoholic hydroxyl group is S—, R— or an R,S-mixture,
R1=hydrogen or lower alkyl Structure 3

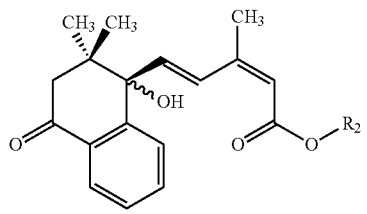

wherein lower alkyl is defined as an alkyl group containing 1 to 4 carbon atoms in a straight or branched chain, which may comprise zero or one ring or double bond when 3 or more carbon atoms are present.

Salts of the above analogs including sodium and potassium salts may be used in this invention.

S-ABA is the preferred compound of the compositions and uses herein and has the structure as follows:

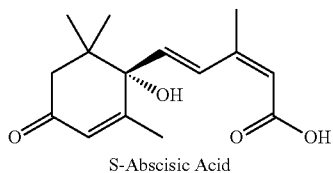 [SMILES: CC1=CC(=O)CC(C)(C)[C@@]1(O)/C=C/C(C)=C\C(=O)O]

S-Abscisic Acid

Compositions and methods of the inventions encompass all isomeric forms of the described abscisic acids, their racemic mixtures, enol forms, solvated and unsolvated forms, analogs, prodrugs, derivatives, including but not limited to esters and ethers, and acceptable salts. Examples of suitable salts that can be used include inorganic salts such as the ammonium, lithium, sodium, potassium, magnesium, and potassium salts and organic amine salts such as the triethanolamine, diethanolamine, dimethylethanolamine, and ethanolamine salts. In one embodiment, the organic amine salt is the triethanolamine salt. In another embodiment, the organic amine salt is the dimethylethanolamine salt. In yet another embodiment, the organic amine salt is the ethanolamine salt. These examples of salts are not limiting as other salts may also be suitable for use in the present invention. One presently preferred salt is the ammonium salt. Other preferred salts are the sodium and potassium salts. The salts may be prepared by contacting the acid form with a sufficient amount of the desired base to produce a salt in the conventional manner. The free acid forms may be regenerated by treating the salt with a suitable dilute aqueous acid solution such as dilute aqueous sulfuric, hydrochloric or phosphoric acid. The free acid forms differ from their respective salt forms somewhat in certain physical properties, such as their solubilities in polar solvents, but the salts are equivalent to their respective free acid forms for purposes of the invention. (See, for example S. M. Berge, et al., "Pharmaceutical Salts," J. Pharm. Sci., 66: 1-19 (1977) which is incorporated herein by reference).

Definitions

The terms "preventing" and "prevention" refer to prophylactic use to reduce the likelihood of a disease, disorder, or condition to which such term applies, or one or more symptoms of such disease, disorder, or condition. It is not necessary to achieve a 100% likelihood of prevention; it is sufficient to achieve at least a partial effect of reducing the risk of acquiring such disease, disorder, or condition.

The term "Animal" refer to any animal, or offspring of animal, who is receiving treatment, is in need of treatment, is taking or receiving treatment for prevention purposes, and/or is being administered the composition. The term "offspring" refers to progeny or descendants of animal, and includes born progeny, fetuses and embryos. "Animals" shall include but not be limited to poultry, including chickens, which includes broilers and layers and male and female breeding stock, geese, duck, turkey, pheasant, cornish hens, swine, cattle, which includes beef and dairy production, sheep, and goats. Further, "Animals" shall also include catfish, carp, tilapia, trout, crayfish, shrimp, lobster, crab, aquatic mammals, salmon, and white fish.

The term "composition" includes a product comprising ABA (and in the specified amounts, if indicated), including products with exogenous or upregulated ABA, as well as any product which results, directly or indirectly, from combination of ABA with specified ingredients in the specified amounts.

The term "administering" or "administration" includes any means for introducing the ABA of the invention and other therapeutic agents, into the body, preferably into the systemic circulation. Examples include but are not limited to oral, buccal, sublingual, pulmonary, ophthalmic, transdermal, transmucosal, intranasal, as well as subcutaneous, intraperitoneal, intravenous, intramuscular injection, transplacental transfer and lactation.

The term "therapeutically effective amount" means an amount of a compound that, when administered to an animal for treating a disease, condition or attaining a desired result, is sufficient to effect such treatment for the disease or desired result. The "therapeutically effective amount" will vary depending on the compound, the disease state being treated or health benefit desired, the severity or the disease treated, the result desired, the age and relative health of the animal, the route and form of administration, the judgment of the attending practitioner, or person attending or caring for animal, and other factors. The amount of ABA that is "effective" will vary from composition to composition, depending on the particular use, the particular ABA, salts, derivatives and analogs thereof, and the like. Thus, it is not always possible to specify an exact "effective amount." However, an appropriate "effective amount" in any individual case may be determined by one of ordinary skill in the art using routine experimentation.

The term "treating" and "treatment" have a commonly understood meaning of administration of a remedy to an animal, or the animal's parent, who has or is suspected of having a disease or a condition, and refer to reversing, alleviating, inhibiting, or slowing the progress of the disease, disorder, or condition to which such terms apply, or one or more symptoms of such disease, disorder, or condition, or preventing or decreasing the chances of a disease, condition, disorder or outcome from occurring, or to increase effects of a specified physiological response or health benefit.

As used herein, the terms "reducing", "suppressing" and "inhibiting" have their commonly understood meaning of lessening or decreasing. As used herein, the term "progression" means increasing in scope or severity, advancing, growing or becoming worse. As used herein, the term "recurrence" means the return of a pre-treatment state after a period of remission.

As used herein, the term "nutraceutical" is commonly understood to mean any substance containing ABA that is a food or liquid, part of a food or liquid, or addition to food or liquid, and that provides medical or health benefits, including the prevention and treatment of disease, or that triggers a physiological response independent or in excess of a substance that does not contain exogenous or upregulated ABA. Such products may range from isolated nutrients, dietary supplements, specific diets, genetically engineered designer foods, herbal products, and processed foods such as cereals, soups, nutritional bars, beverages, tablets, capsules, solutions, emulsions, bars, gels, shakes, yogurts, breads, juices, and other nutraceuticals.

As used herein, all numerical values relating to amounts, weight percentages and the like are defined as "about" or "approximately" each particular value, namely, plus or minus 10%. For example, the phrase "at least 5% by weight" is to be understood as "at least 4.5% to 5.5% by weight." Therefore, amounts within 10% of the claimed values are encompassed by the scope of the claims.

Compositions for Administration

In some embodiments, the compositions of the present invention can be included in a suitable vehicle suitable for oral ingestion. Suitable acceptable carriers include solid fillers or diluents and sterile aqueous or organic solutions. The active compound is present in such compositions in an amount sufficient to provide the desired effect.

Compositions contemplated for use in the practice of the present invention can be used in the form of a solid, a solution, an emulsion, a dispersion, a micelle, a liposome, and the like, wherein the resulting composition contains one or more of the active ingredients in admixture with an organic or inorganic carrier or excipient suitable for nasal, enteral, or parenteral applications.

The active ingredients may be combined, for example, with the usual non-toxic, physiologically acceptable carriers for tablets, pellets, capsules, troches, lozenges, aqueous or oily suspensions, dispersible powders or granules, suppositories, solutions, emulsions, suspensions, hard or soft capsules, caplets or syrups or elixirs and any other form suitable for use. The possible carriers include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents may be used.

In another embodiment, the compositions of the present invention may be formulated for an intranasal, intravenous, transdermal or opthalmic administration. It is within a skill in the art to formulate the compositions for such administration.

In a different embodiment, the compositions of the present invention may be formulated with foodstuffs for oral consumption. In another embodiment, the composition of the present invention may be formulated as a nutritional supplement for consumption, for example as a solid or liquid, such as a tablet, capsule, solution, emulsion, bar, gel, shake or the like. In other embodiments, the compositions of the present invention may be formulated with yogurts, cereals, breads, juices and other nutraceuticals. In more embodiments, the compositions of the present invention may be incorporated with yogurts, cereals, breads, juices and other nutraceuticals including, but not limited to, foodstuffs which provide health benefits.

In a different embodiment, the compositions of the present invention may be formulated in a liquid composition for oral consumption. It is within a skill in the art to formulate the compositions in liquid compositions for oral consumption.

In other embodiments, the compositions of the present invention may be administered through a lactating parent to offspring, through transplacental transfer from parent to offspring, by IV, or in an infant formula for the offspring.

Diseases and Conditions to be Treated with Compositions and Methods of the Invention The invention provides methods of treating and/or preventing a disease or condition comprising administering to an animal in need thereof a therapeutically effective amount of the compositions of the invention.

In another embodiment, the present invention is directed to reproduction and more specifically to methods of increasing post-natal survival rates and weight comprising administering to an animal in need thereof a therapeutically effective amount of ABA.

Another embodiment of the present invention is directed to methods of increasing immunological function comprising administering to an animal or animal in need thereof a therapeutically effective amount of ABA. This may result at least in part due to the reduction in size of the spleen in the animal. The spleen is an organ which plays a role in filtering and recycling blood while platelets and white cells are stored there, all playing a role with the immune system.

A preferred range of a therapeutically effective amount of ABA for the various methods is from about 0.1 mg/kg/day to about 1000 mg/kg/day. A more preferred range of a therapeutically effective amount of ABA is from about 10 mg/kg/day to about 1000 mg/kg/day. An especially preferred range of a therapeutically effective amount of ABA is from about 50 mg/kg/day to about 500 mg/kg/day. An especially preferred range of a therapeutically effective amount of ABA is from about 50 mg/kg/day to about 200 mg/kg/day.

The preferred composition comprises S-ABA.

One embodiment of the present invention is liquid compositions that can be prepared as either ready-to-use dilutions or dilutable concentrates. The embodiment of the present invention can be a solution containing from 0.5% to as much as 50% by weight of ABA. The dilutable concentrates can be diluted into water directly to a final application concentration or to any intermediate dilution, without risk of precipitation of the active ingredient. The aqueous formulations according one embodiment of the present invention are inexpensive to manufacture, safe to handle and use, and the ABA active ingredient is stable under storage and shipping conditions. A person having ordinary skill in the art would be able to determine how to prepare the final aqueous solution concentration for direct application to animals without undue experimentation, without any chance of causing precipitation of the active ingredient, and without long and laborious stirring to bring the active ingredient into solution.

Compositions of the present invention may be prepared as a single unit dose or as a plurality of single unit doses. As used herein, a "unit dose" means a discrete amount of the composition comprising a predetermined amount of the active ingredient. The amount of the active ingredient is generally equal to the dosage of the active ingredient that would be administered to an animal or a fraction thereof.

Compositions of the present invention may be liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween® (Tween is a registered trademark of Uniqema Americas, LLC) 20™, Tween® 80™ Pluronic® (Pluronic is a registered trademark of BASF Corporation) F68™, bile acid salts), solubilizing agents (e.g., glycerol, polyethylene glycerol), anti-oxidants (e.g., ascorbic acid, sodium metabisulfite), preservatives (e.g., Thimerosal™, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

Further, as used herein acceptable carriers are well known to those skilled in the art and include, but are not limited to, 0.01-0.1 M and preferably 0.05M phosphate buffer or 0.9% saline. Additionally, such acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Controlled or sustained release compositions according to the invention include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors. Other embodiments of the compositions according to the invention incorporate particulate forms, protective coatings, protease inhibitors or permeation enhancers for various routes of administration, including parenteral, pulmonary, nasal and oral.

Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds. Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

The preparation can comprise the ABA, alone, or can further include a pharmaceutically acceptable carrier, and can be in solid or liquid form such as tablets, powders, capsules, pellets, solutions, suspensions, elixirs, emulsions, sprays, gels, creams, or suppositories, including rectal and urethral suppositories. Pharmaceutically acceptable carriers include gums, starches, sugars, cellulosic materials, and mixtures thereof. The preparation containing the ABA can be administered to an animal by, for example, subcutaneous implantation of a pellet. The preparation can also be administered by intranasal, intravenous, intraarterial, or intramuscular injection of a liquid preparation. Administration can also be accomplished by use of a rectal suppository or a urethral suppository.

The preparations administrable by the invention can be prepared by known dissolving, mixing, granulating, or tablet-forming processes. For oral administration, ABA and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders such as acacia, cornstarch, gelatin, with disintegrating agents such as cornstarch, potato starch, alginic acid, or with a lubricant such as stearic acid or magnesium stearate.

Examples of suitable oily vehicles or solvents are vegetable or animal oils such as sunflower oil or fish-liver oil. Preparations can be effected both as dry and as wet granules. For parenteral administration (subcutaneous, intravenous, intra-arterial, or intramuscular injection), the ABA and the like are converted into a solution, suspension, or emulsion, if desired with the substances customary and suitable for this purpose, for example, solubilizers or other auxiliaries. Examples are sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

The preparation of compositions which contain an active component is well understood in the art. Such compositions may be prepared as injectables, either as liquid solutions or suspensions; however, solid forms suitable for solution in, or suspension in, liquid prior to injection can also be prepared. The preparation can also be emulsified. Active therapeutic ingredients are often mixed with excipients which are pharmaceutically acceptable and compatible with the active ingredient. Suitable excipients are, for example, water, saline, dextrose, glycerol, ethanol, or the like or any combination thereof.

In addition, the composition can contain minor amounts of auxiliary substances such as wetting or emulsifying agents, pH buffering agents which enhance the effectiveness of the active ingredient.

Animal Feed

The composition of the invention may preferably take the form of animal feed and includes protein, fat, fiber, calcium, and phosphorous. A preferred feed would include corn and/or wheat, soybean meal, fat, animal by-product, meat and bone meal, and vitamins and minerals.

ABA can be initially mixed into a premix. The term "premix" is intended to mean a feed composition that is prepared as an initial mix containing the active ingredient and, for example, a carrier, and is then blended into the final feed. In the present invention, it is generally suggested that, for ease of calculation and use, the premix is blended with about one metric ton (MT) of conventional feed, with the result that the necessary dosage requirements of the ABA are provided to the animals. When preparing one metric ton (MT) of finished feed, the premix of the invention preferably comprises about 1 to 2000, and more preferably, about 5 to 500, grams of ABA. Carriers for use in a premix are well known by those having skill in the art, and appropriate concentrations can be readily determined.

The ABA may be added to the carrier as a dry powder or as a liquid solution or suspension. When added as a liquid, the ABA may be dissolved or suspended in a liquid with stirring at room temperature. Such liquid may be water or a suitable solvent or another product used for animal feed that is already in liquid form. Because of ABA's liquid solubility characteristics, it may form a suspension. A predetermined amount of ABA is then added to the conventional premix, and will not overly wet it. Once the premix is prepared, the premix is then added to the final feed, preferably at a rate in the range of one quarter of a pound (lb.) to five pounds (lbs.) of premix to one metric ton (MT) of feed, to supply daily requirements of the ABA for the poultry.

The ABA solid or solution or liquid suspension can be added directly to the premix material, and then mixed. Mixing can be accomplished by any known means, such as by a standard horizontal or vertical blender. Mixing time will again vary depending upon the particular ingredients of the premix, and can take as long as is necessary to assure that the ingredients are thoroughly mixed.

The premix is then incorporated into the feed to be fed to the poultry. In a more preferred embodiment, ABA is blended with the carrier to form the premix, and the premix is directly blended into the final feed. While there is no evidence that use of the higher amounts would cause any toxicity problems in treated poultry, it will affect cost considerations. Because the premix generally will be added to one-ton charges of feed (as is common in the industry), the correspondence between one gram of ABA added to the premix yields about 1 ppm concentration of ABA in the feed. Thus, 5 grams of ABA added to one pound of premix, which in turn is added to one metric ton (MT) of feed, yields about a 5 ppm effective ABA concentration.

While the ABA can be mixed with a premix material prior to incorporation into the finished feed, the appropriate amount of ABA may be directly blended into or sprayed upon the feed. The preferred additive range of ABA in finished feed, whether added directly or via a premix, is about 1 to 2000 grams per metric ton (MT) of feed; more preferably about 5 to 500 grams per metric ton (MT) of feed.

Feed is conventionally prepared in a large bin or mixer in which the feed ingredients are added in descending weight order according to their prevalence in the ultimate feed mixture. Thus, cracked or ground grain would be the primary ingredient. Minor ingredients are then added. Micro-ingredients are added last. These include vitamins, drugs, growth promoters, antibiotics, and, in the present case, ABA. Thus, ABA can be one of the micro-ingredients and is added to the feed in the final blending step. The feed is blended for conventional time periods.

The feed comprising the ABA is fed to livestock and fish in standard form, such as a mash, crumble or pellet, and at standard feed dosage ranges and rates.

Another embodiment of the present invention is liquid compositions that can be prepared as either ready-to-use dilutions or dilutable concentrates. The embodiment of the present invention can be a solution containing from 0.5% to as much as 50% by weight of ABA. The dilutable concentrates can be diluted into water directly to a final application concentration or to any intermediate dilution, without risk of precipitation of the active ingredient. The aqueous formulations according to one embodiment of the present invention are inexpensive to manufacture, safe to handle and use, and the ABA active ingredient is stable under storage and shipping conditions. A person having ordinary skill in the art would be able to determine how to prepare the final aqueous solution concentration for direct application to animals without undue experimentation, without any chance of causing precipitation of the active ingredient, and without long and laborious stirring to bring the active ingredient into solution.

Another embodiment of the present invention is an ABA water solution that serves as a drinking source of water for the animals. Such supplemented water solution could be prepared by dissolving dry powder ABA in drinking water or by using a liquid solution or suspension concentrate of ABA. The preferred additive range of ABA in drinking water is about 1 to 2000 parts per million (ppm) or about 1 to 2000 milligrams of ABA per liter of water; more preferably about 5 to 500 parts per million (ppm) or about 5 to 500 milligrams of ABA per liter of water. A person having ordinary skill in the art would be able to determine how to prepare the final aqueous solution for direct application to animals without undue experimentation, without any chance of causing precipitation of the active ingredient, and without long and laborious stirring to bring the active ingredient into solution.

In another embodiment of the present invention ABA can be applied directly onto animal feed once it has been prepared. For example, as can be the practice with some enzymes, the ABA can be applied directly to the finished feed. In a preferred embodiment, an aqueous solution of ABA is sprayed onto the finished feed in its final form, such as a pellet, prior to delivering the feed to the animals.

The advantageous properties of this invention can be observed by reference to the following examples that illustrate the invention. These examples are provided for the purposes of illustration and are not intended to limit the scope of the present invention.

EXAMPLES

Tests were conducted with (S)-(+)-abscisic acid in accordance with standard guidelines and procedures as evidenced by EPA Subchronic Toxicity Test Guidelines: 870.3050—Repeated Dose 28-Day Oral Toxicity Study in Rodents (July 2000); 870.3100—90-Day Oral Toxicity in Rodents (August 1998); 870.3650—Combined Repeated Dose Toxicity Study with the Reproduction/Developmental Toxicity Screening Test (July 2000); and 870.3200—21/28-Day Dermal Toxicity (August 1998), as well as Organization for Economic Co-operation and Development (OECD) Guidelines for the Testing of Chemicals including: Test No. 407: Repeated Dose 28-day Oral Toxicity Study in Rodents; Test No. 408: Repeated Dose 90-Day Oral Toxicity Study in Rodents; Test No. 416: Two-Generation Reproduction Toxicity; and Test No. 410: Repeated Dose Dermal Toxicity: 21/28-day Study.

Examples of the data from these studies are presented below.

Two Generation Reproduction Toxicity Study

This study was conducted to determine the potential adverse effects of the test substance on reproduction in a 2-generation study. This included determining the effects of the test substance on male and female reproductive processes, including gonadal function, estrous cyclicity, mating behavior, conception, gestation, parturition, lactation, weaning, and on growth and development of the offspring. A minimum of 1 litter was produced in each generation.

Three groups of male and female were offered ABA, continuously in the diet for at least 70 consecutive days prior to mating. Target tests substance concentrations were 10,000, 15,000, and 20,000 ppm for the F0 and F1 generations. A concurrent control group of 30 rats/sex was offered the basal diet continuously throughout the study. F0 animals were approximately 7 weeks of age at the initiation of test diet administration. The test diet was administered to the offspring selected to become the F1 generation following weaning. The F0 and F1 males continued to receive the test substance throughout mating and continuing through the day prior to euthanasia. The F0 and F1 females continued to receive the test substance throughout mating, gestation, and lactation, and through the day of euthanasia. For both generations (F1 and F2), 8 pups per litter (4 per sex, when possible) were selected to reduce the variability among the litters. Offspring (30/sex/group, if possible) from the pairing of the F0 animals were selected to constitute the F1 generation. F0 males and females were exposed for 127-130 consecutive days and F1 males and females were exposed for 178-186 consecutive days.

All animals were observed twice daily for appearance and behavior. Clinical observations, body weights, and food consumption were recorded at appropriate intervals for males throughout the study and for females prior to mating and during gestation and lactation. All F0 and F1 females were allowed to deliver and rear their pups until weaning on lactation day 21. Clinical observations, body weights, and sexes for F1 and F2 pups were recorded at appropriate intervals. Nonselected F1 pups and all surviving F2 pups were necropsied. Selected organs were weighed from 1 pup/sex/litter from F1 and F2 pups that wee necropsied. Each surviving F0 and F1 parental animal received a complete detailed gross necropsy following the completion of weaning of the F1 and F2 pups, respectively; selected organs were weighed. Spermatogenic endpoints were recorded for all F0 and F1 males, and ovarian primordial follicle counts were recorded for all F0 and F1 females in the control and high-exposure groups and all F0 and F1 females suspected of reduced fertility. Designated tissues from all F0 and F1 parental animals were examined microscopically.

Reproduction

Table 1 demonstrates increased postnatal survival rates of offspring in response to S-ABA treatments.

TABLE 1

POSTNATAL SURVIVAL (% PER LITTER)

| DOSE (PPM) | | 0 (RELATIVE TO # BORN) | 0-1 | 1-4 (PRE-SELECTION) | 4 (POST-SELECTION)-7 | 7-14 | 14-21 | BIRTH-4 (PRE-SELECT) | 4 (POST-SELECT)-21 |
|---|---|---|---|---|---|---|---|---|---|
| 0 | MEAN | 98.4 | 98.0 | 99.5 | 98.6 | 99.5 | 100.0 | 95.9 | 98.1 |
| | N | 26 | 26 | 26 | 26 | 26 | 26 | 26 | 26 |
| 10,000 | MEAN | 99.7 | 100.0 | 98.9 | 99.5 | 100.0 | 100.0 | 98.6 | 99.5 |
| | N | 25 | 25 | 25 | 25 | 25 | 24 | 25 | 24 |
| 15,000 | MEAN | 96.1 | 98.5 | 98.5 | 99.6 | 98.7 | 100.0 | 93.2 | 98.2 |
| | N | 29 | 28 | 28 | 28 | 28 | 28 | 29 | 28 |
| 20,000 | MEAN | 98.5 | 99.7 | 98.5 | 98.5 | 99.5 | 100.0 | 96.8 | 98.0 |
| | N | 25 | 25 | 25 | 25 | 25 | 25 | 25 | 25 |

As a result of this test data, we see that S-ABA increases postnatal offspring survival rates. For instance, by days 4 through 7, a 10,000 ppm dose resulted in an increase in mean survival from 98.6% to 99.5% in rats.

Table 2 demonstrates increased weight gain of offspring in response to S-ABA treatments.

TABLE 2

OFFSPRING WEIGHT (grams)

| DOSE (PPM) | | | POSTNATAL DAY | | | | |
|---|---|---|---|---|---|---|---|
| | | | 1 | 4 | 7 | 14 | 21 |
| 0 | MALE | MEAN | 6.9 | 9.1 | 14.0 | 29.7 | 46.8 |
| | | N | 26 | 26 | 26 | 26 | 26 |
| | FEMALE | MEAN | 6.5 | 8.5 | 13.0 | 28.2 | 44.4 |
| | | N | 26 | 26 | 26 | 26 | 26 |
| 10,000 | MALE | MEAN | 7.1 | 9.7 | 15.2 | 30.9 | 47.9 |
| | | N | 25 | 25 | 25 | 25 | 24 |
| | FEMALE | MEAN | 6.6 | 9.1 | 14.3 | 29.9 | 45.5 |
| | | N | 25 | 25 | 25 | 25 | 24 |
| 15,000 | MALE | MEAN | 6.9 | 9.3 | 14.7 | 30.8 | 47.8 |
| | | N | 28 | 28 | 28 | 28 | 28 |
| | FEMALE | MEAN | 6.6 | 8.8 | 14.0 | 29.8 | 45.8 |
| | | N | 28 | 28 | 28 | 28 | 28 |
| 20,000 | MALE | MEAN | 7.0 | 9.3 | 15.1 | 31.2 | 48.1 |
| | | N | 25 | 25 | 25 | 25 | 25 |
| | FEMALE | MEAN | 6.6 | 8.8 | 14.5 | 30.5 | 46.6 |
| | | N | 24 | 24 | 24 | 24 | 24 |

As a result of this test data, we see that S-ABA increases offspring weight gain. For instance, by day 21, a 10,000 ppm dose resulted in an increase in mean offspring weight from 46.8 grams to 47.9 grams in male rats. The corresponding increase in mean offspring weight for female rats was from 44.4 grams to 45.5 grams.

This result is also suggestive that ABA could be substituted for prophylactic antibiotics that are often utilized in animal reproduction.

Table 3 demonstrates decreased offspring mortality levels in response to S-ABA treatments.

TABLE 3

| DOSE (PPM) | Offspring Born | FOUND DEAD |
|---|---|---|
| 0 | 328 | 15 |
| 10,000 | 322 | 4 |
| 15,000 | 375 | 15 |
| 20,000 | 327 | 11 |

As a result of this test data, we see that SABA decreases offspring mortality. For instance, a 10,000 ppm dose resulted in a decrease from 4.57% to 1.24%.

Table 4 demonstrates increased mean live offspring per litter in response to S-ABA treatments.

TABLE 4

| | Dose (PPM) | | | |
|---|---|---|---|---|
| | 0 | 10,000 | 15,000 | 20,000 |
| Mean Live Offspring Born | 11.8 | 12.3 | 13.1 | 12.3 |
| N | 25 | 27 | 27 | 27 |

As a result of this test data, we see that SABA increases the number of live offspring per litter. For instance, a 15,000 ppm dose resulted in an increase in mean offspring number from 11.8 to 13.1 per litter.

Further supporting data can be seen below in Tables 2 and 3 showing that at necropsy fetus numbers and follicle size increase with the addition of SABA.

TABLE 5

FETAL DATA AT SCHEDULED NECROPSY

| GROUP | | SEX | | VIABLE FETUSES |
|---|---|---|---|---|
| | | MALE | FEMALE | |
| 1 | N | 154 | 179 | 343 |
| 0 MG/KG/DAY | MEAN | 5.5 | 7.2 | 13.7 |
| 2 | N | 187 | 181 | 368 |
| 500 MG/KG/DAY | MEAN | 7.5 | 7.2 | 14.7 |
| 3 | N | 188 | 166 | 354 |
| 750 MG/KG/DAY | MEAN | 7.5 | 6.6 | 14.2 |
| 4 | N | 170 | 208 | 378 |
| 1,000 MG/KG/DAY | MEAN | 6.8 | 8.3 | 15.1 |

TABLE 6

OVARIAN PRIMORDIAL FOLLICLE COUNTS
FEMALES

| | GROUP | | | |
|---|---|---|---|---|
| | 0 PPM | 10,000 PPM | 15,000 PPM | 20,000 PPM |
| | PRIMORDIAL FOLLICLES | | | |
| MEAN | 120.1 | 257.5 | 214.0 | 270.3 |
| N | 30 | 5 | 1 | 30 |

Immune System Health

Two-generation reproductive toxicity studies of S-ABA in rats demonstrated spleen weight reduction in both males and second generation pups as seen in Table 7 and 8.

TABLE 7

MALES

| | GROUP | | | |
|---|---|---|---|---|
| | 0 PPM | 10,000 PPM | 15,000 PPM | 20,000 PPM |
| | SPLEEN WEIGHT (GRAMS) | | | |
| MEAN | 1.00 | 0.98 | 0.97 | 0.92 |
| % DIFFERENCE | | −2.0 | −3.0 | −8.9 |
| N | 30 | 30 | 28 | 30 |

TABLE 8

SUMMARY OF ORGAN WEIGHTS AND
RELATIVE ORGAN WEIGHTS
SECOND GENERATION PUPS

| | GROUP | | | |
|---|---|---|---|---|
| | 0 PPM | 10,000 PPM | 15,000 PPM | 20,000 PPM |
| | SPLEEN WEIGHT (GRAMS) | | | |
| MEAN | 0.2334 | 0.1989 | 0.1918 | 0.1979 |
| % DIFFERENCE | | −14.8 | −17.8 | −15.2 |
| N | 25 | 25 | 27 | 27 |

Reduced spleen size, as shown in the tables/data above, may be directly related to improved health and improved mortality shown in the Reproduction tables/data above.

What is claimed is:

1. A method of improving post-natal weight gain of animal offspring comprising administering to the offspring from about 10 mg/kg/day to about 1000 mg/kg/day of abscisic acid (ABA).

2. The method of claim 1 wherein the therapeutically effective amount of ABA is from about 50 mg/kg/day to about 500 mg/kg/day.

3. The method of claim 1 wherein the therapeutically effective amount of ABA is from about 50 mg/kg/day to about 200 mg/kg/day.

\* \* \* \* \*